United States Patent [19]

Griffin, III

[11] Patent Number: 5,807,324
[45] Date of Patent: Sep. 15, 1998

[54] STEERABLE CATHETER

[75] Inventor: Joseph C. Griffin, III, Atco, N.J.

[73] Assignee: ProCath Corporation, West Berlin, N.J.

[21] Appl. No.: 625,866

[22] Filed: Apr. 1, 1996

[51] Int. Cl.$^6$ .................................................. A61M 37/00
[52] U.S. Cl. ........................... 604/95; 604/264; 604/280; 607/116
[58] Field of Search ................................. 604/21, 95, 280, 604/281, 164, 264; 128/656–658, 772; 607/115, 116, 148

[56] References Cited

U.S. PATENT DOCUMENTS

| | | | |
|---|---|---|---|
| 4,033,331 | 7/1977 | Guss et al. ........................... | 604/95 X |
| 4,790,331 | 12/1988 | Okada et al. .......................... | 128/772 |
| 4,911,174 | 3/1990 | Pederson et al. ...................... | 128/695 |
| 4,925,445 | 5/1990 | Sakamoto et al. ...................... | 604/95 |
| 5,109,830 | 5/1992 | Cho ....................................... | 604/95 X |
| 5,207,648 | 5/1993 | Gross ..................................... | 604/164 |
| 5,308,324 | 5/1994 | Hammerslag et al. .................. | 604/95 |
| 5,324,284 | 6/1994 | Imran ..................................... | 606/15 |
| 5,345,937 | 9/1994 | Middleman et al. .................... | 128/657 |
| 5,364,352 | 11/1994 | Cimino et al. ........................... | 604/95 |
| 5,383,852 | 1/1995 | Stevens-Wright ........................ | 604/95 |
| 5,405,375 | 4/1995 | Ayers et al. .............................. | 607/122 |
| 5,423,772 | 6/1995 | Lurie et al. .............................. | 604/282 |
| 5,439,006 | 8/1995 | Brennen et al. ......................... | 128/772 |
| 5,445,148 | 8/1995 | Jaraczewski et al. ................... | 128/642 |

Primary Examiner—Wynn Wood Coggins
Assistant Examiner—N. Kent Gring
Attorney, Agent, or Firm—Norman E. Lehrer

[57] ABSTRACT

A steerable catheter comprises an elongated flexible member that has a proximal end and a distal end. The flexible member further has a plurality of lumens which extend from the proximal end to the distal end thereof. In one embodiment, a stylet is slidably receivable in one of the lumens and has a bent portion formed along the length thereof. The bent portion causes a segment of the flexible member in contact with the same to bend. In a second embodiment, the stylet is straight and the flexible member has a bent portion. In yet another embodiment, both the stylet and flexible member include a bent portion. A plurality of electrodes are secured around the periphery of the flexible member in a predetermined pattern. A plurality of electrical leads extend through the proximal end of the flexible member and through a corresponding one of the plurality of lumens. The electrical leads are adapted to supply electrical current to the electrodes.

8 Claims, 2 Drawing Sheets

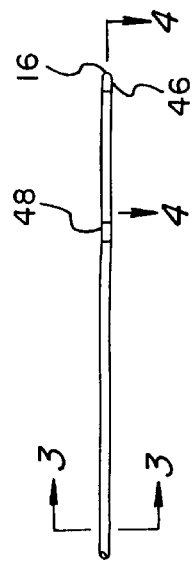
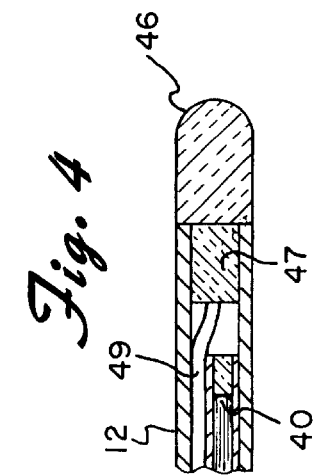
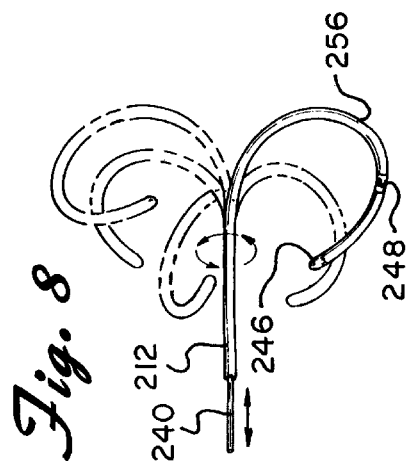
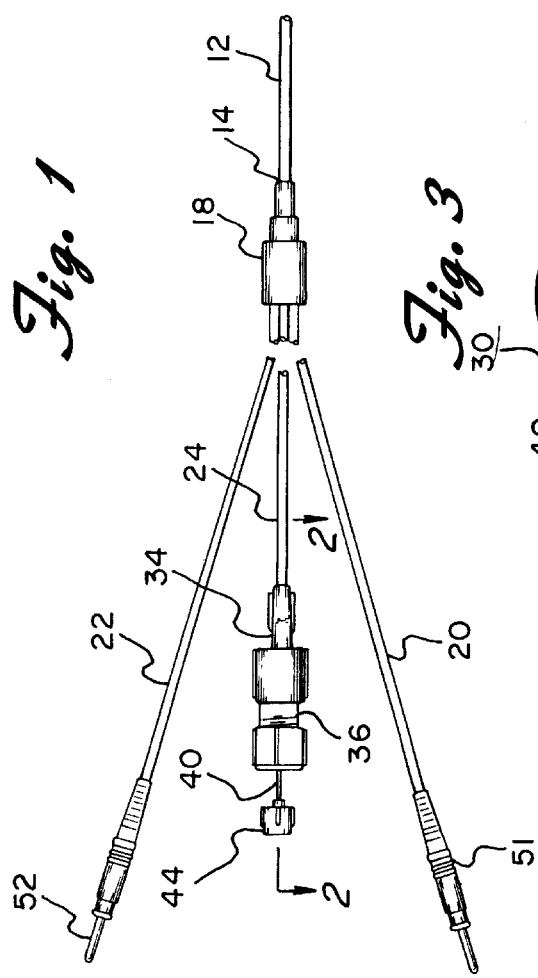
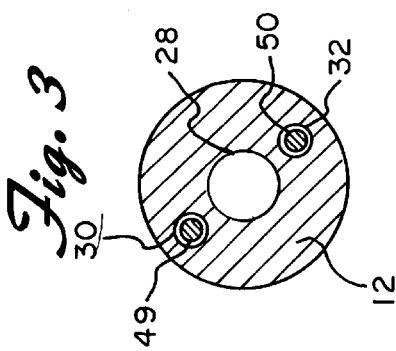

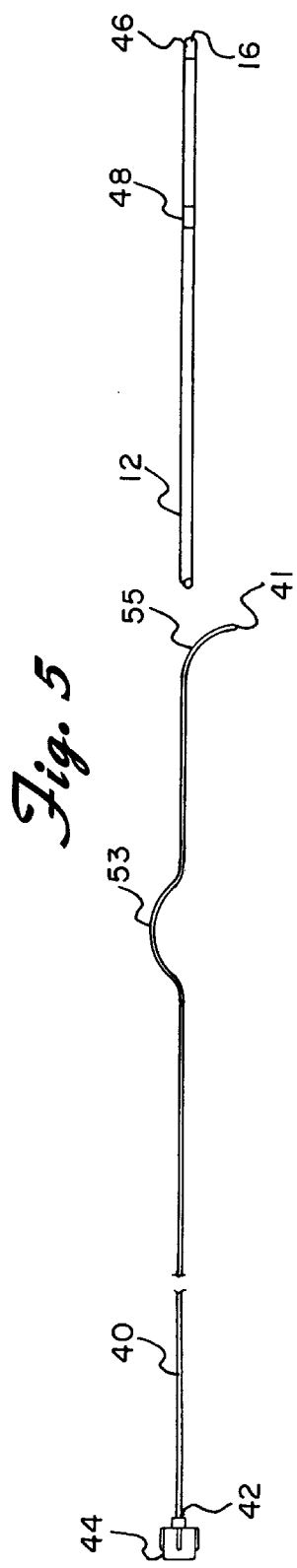
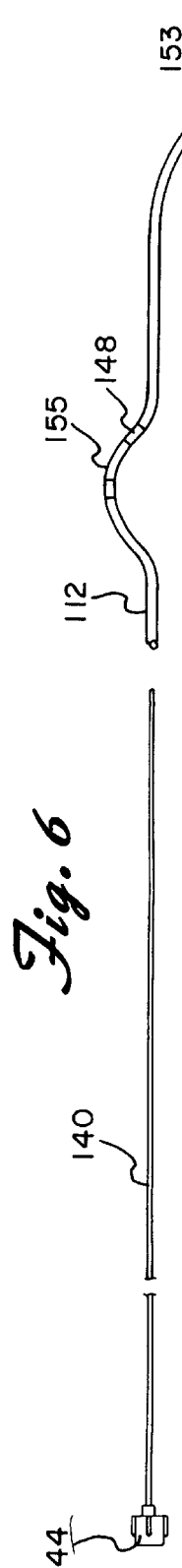
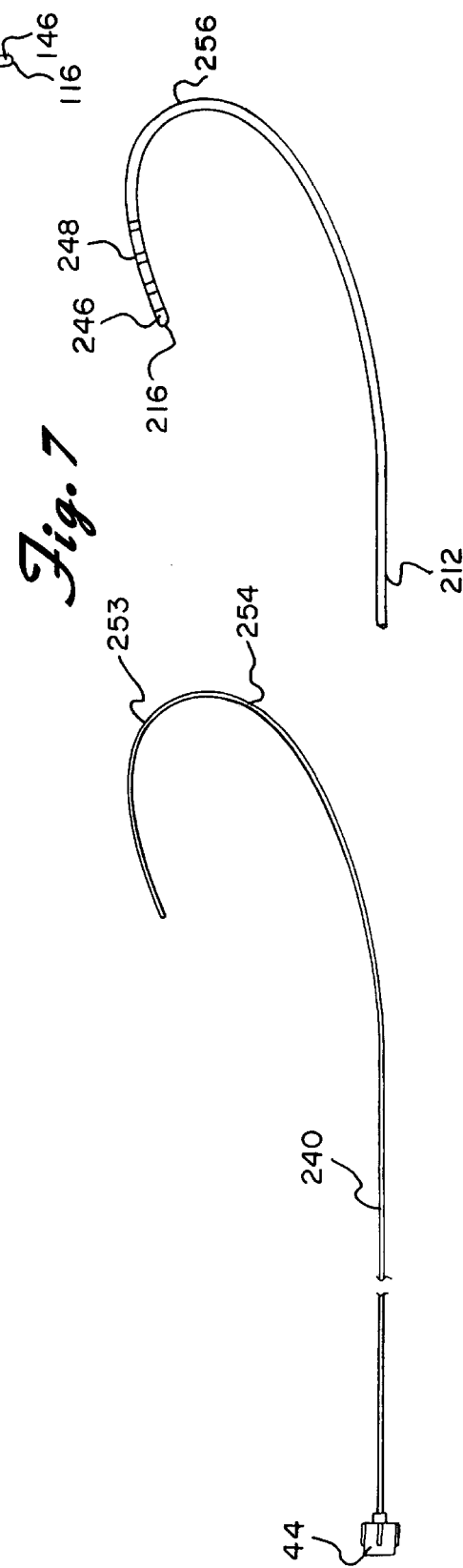

STEERABLE CATHETER

BACKGROUND OF THE INVENTION

The present invention relates generally to steerable catheters and, more particularly, toward a steerable catheter that can be easily maneuvered through a human heart.

Steerable electrode catheters are widely used today for the purpose of intracardiac pacing, stimulation, sensing, RF ablation, or ECG recording. The success of such procedures is dependant on the physician's ability to properly place the catheter in the patient's heart.

Many such procedures often require physicians to utilize two separate catheters in order to ensure the proper placement of electrodes in the heart. The use of two catheters is necessitated by the inability of existing catheters to be maneuvered in certain inaccessible areas of the heart. For example, the path between the high right atrium, the tricuspid valve and the ventricular apex includes several sharp bends and direction changes. Such a path makes it virtually impossible for a single existing catheter to be properly positioned in both the high right atrium and the ventricular apex.

A typical steerable catheter is designed to be inserted through the skin of the patient, into a vein or artery and be advanced until the tip of the catheter is positioned within the heart. Known steerable catheters include a bendable tip so that the catheter can be maneuvered through various bends and changes in direction. Typically, these catheters include a wire which has one end secured to the catheter tip and an opposite end secured to a handle. In order to bend the catheter tip, the physician manipulates the handle to pull the wire and thereby curve the catheter. Such devices are relatively complicated and expensive to manufacture.

SUMMARY OF THE INVENTION

The present invention is designed to overcome the deficiencies of the prior art discussed above. It is an object of the invention to provide a steerable catheter that can be easily maneuvered through a human heart.

It is a further object to provide such a catheter which is relatively inexpensive to manufacture.

It is yet another object of the invention to provide such a catheter which can be simultaneously positioned in both the ventricular apex and the atrium.

In accordance with the illustrative embodiments, demonstrating features and advantages of the present invention, there is provided a steerable catheter. The steerable catheter comprises an elongated flexible member that has a proximal end and a distal end. The flexible member further has a plurality of lumens which extend from the proximal end to the distal end thereof. In one embodiment, a stylet is slidably receivable in one of the lumens and has a bent portion formed along the length thereof. The bent portion causes a segment of the flexible member in contact with the same to bend. In a second embodiment, the stylet is straight and the flexible member has a bent portion. In yet another embodiment, both the stylet and flexible member include a bent portion. A plurality of electrode means are secured around the periphery of the flexible member in a predetermined pattern. A plurality of electrical leads extend through the proximal end of the flexible member and through a corresponding one of the plurality of lumens. The electrical leads are adapted to supply electrical current to the electrode means.

Other objects, features and advantages of the invention will be readily apparent from the following detailed description of a preferred embodiment thereof taken in conjunction with the drawings.

BRIEF DESCRIPTION OF THE DRAWINGS

For the purpose of illustrating the invention, there is shown in the accompanying drawings forms which are presently preferred; it being understood that the invention is not intended to be limited to the precise arrangements and instrumentalities shown.

FIG. 1 is a side plan view of the present invention;

FIG. 2 is a cross-sectional view taken along lines 2—2 of FIG. 1;

FIG. 3 is an enlarged cross-sectional view taken along lines 3—3 of FIG. 1;

FIG. 4 is cross-sectional view taken along lines 4—4 of FIG. 1;

FIG. 5 is a plan view of a curved stylet and a straight catheter;

FIG. 6 is a plan view of a straight stylet and a curved catheter;

FIG. 7 is a plan view of a curved stylet and a curved catheter, and

FIG. 8 is a view of the catheter tip of FIG. 7 shown moving about two planes.

DETAILED DESCRIPTION OF THE PREFERRED EMBODIMENT

Referring now to the drawings in detail wherein like reference numerals have been used throughout the various figures to designate like elements, there is shown in FIG. 1 a steerable catheter constructed in accordance with the principles of the present invention and designated generally as 10. The steerable catheter is adapted to be easily maneuvered through a human heart. It should be understood, however, that the features of the invention could be used with other types of catheters.

The catheter 10 includes an elongated flexible member 12. A preferred material for the flexible member is extruded polyether block amide of the type sold by Atochem North America, Inc. under the trademark PEBAX. However, the flexible member can be comprised of other polymeric materials which have excellent memory characteristics such as polyurethane, silicone rubber and plasticized PVC. Additionally, the flexible member can be reinforced with a braided layer of stainless steel in order to increase the torsional rigidity of the same. The flexible member 12 is preferably 90 cm long (+/−10 cm) and has an outer diameter of approximately 2 mm (6 French).

Member 12 has a proximal end 14 and a distal end 16 (FIGS. 1 and 2). A manifold 18 is secured around the proximal end 14. Extending outwardly from the manifold 18 is a proximal electrical lead 20, a distal pacing/sensing electrical lead 22, and a stylet tube 24.

As shown best in FIG. 3, a central lumen 28 is formed through the center of the flexible member 12. The central lumen preferably has a diameter of approximately 0.71 mm. A plurality of lumens 30 and 32 are also formed through the flexible member 12 and have a preferred diameter of approximately 0.355 mm.

Referring to FIGS. 1 and 2, the end of the stylet tube 24 positioned within the manifold 18 is connected to the central lumen 28. The opposing free end of the stylet tube 24 preferably terminates with a female connecting terminal 34, commonly referred to as a luer-lock hub extension. A compression fitting 36 is mated with the female connecting terminal 34. A Touhy-Borst compression fitting is preferably utilized and is available from Medical Disposables International, Inc. of West Conshahocken, Pa.

The steerable catheter 10 includes a stylet 40 which is slidably receivable in the central lumen 28 of the flexible member 12. The stylet 40 is significantly stiffer than the flexible member 12 and includes a first end 41 and a second end 42 (FIGS. 2 and 5). Specifically, the first end 41 of the stylet is passed through the compression fitting 36, through the female connecting terminal 34, through the stylet tube 24, and into the central lumen 28. The opposing end 42 of the stylet 40 extends outwardly from the compression fitting 36 (FIG. 2). The stylet 40 is preferably coated with tetrafluoroethylene (TEFLON®), is approximately 97.5 cm long (+/−5 cm) and has a diameter of approximately 0.5 mm. The Touhy-Borst compression fitting 36 allows a physician to hold the stylet in a fixed position in a manner well known in the art.

Secured to the end 42 of the stylet 40 is an orbit knob 44. The orbit knob 44 provides a means to grasp the stylet 40 so that the stylet can be rotated and/or positioned further into or out of the flexible member 12 in order to properly position the catheter.

A plurality of electrodes are mounted on the flexible member 12 of the catheter and are adapted to receive electrical impulses for the purpose of intracardiac pacing, stimulation, sensing, RF ablation, or ECG recording. In a preferred embodiment, an electrode cap 46 is secured to the distal end 16 of the flexible member 12. Similarly, an electrode band 48 is secured adjacent the electrode cap 46 on the flexible member 12. The electrode cap and the electrode band are each preferably 2 mm long and are composed of a platinum-iridium alloy.

The distal electrical lead 22 transmits electrical impulses to the electrode cap 46 through a low resistance conductive wire 49 which passes through the lumen 30 and is connected to an electrode cap shaft 47 as illustrated in FIG. 4. Similarly, the proximal electrical lead 20 transmits electrical impulses to the electrode band 48 through a low resistance conductive wire 50 which passes through the lumen 32 (FIG. 3). The electrical impulses are generated by a power source well known in the art and are passed through contact pins 51 and 52 which extend from corresponding electrical leads 20 and 22. While only two electrodes are specifically described, it should be noted that numerous other electrodes could also be secured to the catheter along the length thereof at a variety of different locations.

In the embodiment shown in FIG. 5, the stylet 40 has a bent portion 53 formed along the length thereof and a J-shaped tip 55 formed adjacent the first end 41 thereof. In use, the physician grasps the orbit knob to move the stylet further into or out of the flexible member, or to rotate the stylet so that the electrode cap 46 and the electrode band 48 are placed in the desired area of the heart. More specifically, as the stylet is moved further into the flexible member 12, the J-shaped tip 55 causes the flexible member 12 to similarly bend since the stylet is stiffer than the flexible member. This allows the catheter to be properly maneuvered within the heart and also allows the electrode cap 46 to be properly positioned. Similarly, the bent portion 53 of the stylet 40 allows the electrode band 48 to be properly positioned in the heart. As the stylet 40 is withdrawn from the flexible member 12, the restoring force in the flexible member causes the same to straighten out into its original form.

In the embodiment shown in FIG. 6, a straight stylet 140 is shown. A curve 153 is formed adjacent the distal end 116 of the flexible member 112. Accordingly, as the end of the straight stylet 140 is moved into the flexible member 112 toward the distal end 116 thereof, the tip of the flexible member is straightened out. This allows the catheter 10 to be steered through the patient's body. As the stylet 140 is withdrawn from the flexible member 12, the restoring force of the flexible member causes the same to once again curve. As stated above, the orbit knob 44 is utilized by the physician to properly position the electrode cap 146 and the electrode band 148 in the heart. A bent portion 155 can also be formed along the length of the flexible member 112 in order to further ensure the proper positioning of the electrode band 48 in the heart.

In the embodiment shown in FIGS. 7 and 8, a curved stylet 240 is shown. The curved stylet 240 preferably has two bent portions 253 and 254 formed adjacent the end thereof. Bent portion 253 is formed along one plane, while bent portion 254 is formed along a different plane. A flexible member 212 having a preformed curved tip 256 is associated with the curved stylet 240. The tip of the flexible member 212 is preferably J-shaped. As the end of the stylet 240 is moved into the flexible member through the central lumen, the bent portions 253 and 254 cause the tip of the flexible member to rotate 180° around the major axis of the stylet so that the physician can control the direction in which he or she rotates the J-shaped tip 256 of the flexible member 212. Again, this allows the electrode cap 246 and the electrode band 248 to be properly positioned in the heart (FIG. 8).

In order to facilitate an understanding of the principles associated with the foregoing steerable catheter, its operation will now be briefly described. As stated above, the steerable catheter 10 can be used to provide electrical impulses to specific portions of a heart for the purpose of intracardiac pacing, stimulation, sensing, RF ablation, or ECG recording. In use, the catheter 10 is inserted percutaneously through the internal jugular vein or the subclavian vein. The catheter is then guided into the patient's heart. The various stylet/flexible member configurations illustrated in FIGS. 5, 6 and 7 and discussed above, allow the electrode cap 46 and electrode band 48 to be properly positioned in the heart.

By way of example, a catheter including the stylet/flexible member combination shown in FIG. 7 can be utilized to facilitate the maneuvering of the catheter 10 from the high right atrium, through the tricuspid valve down into the ventricular apex. This is accomplished by advancing the bent portions 253 and 254 of the stylet 240 toward the distal end 216 of the flexible member 212. Since the stylet is bent in two planes (bent portion 253 and bent portion 254), the advancing of the stylet causes the tip of the flexible member to rotate in the manner shown in FIG. 8.

By way of an additional example, a catheter including the stylet/flexible member combination shown in FIG. 5 can be utilized to simultaneously position the catheter in both the ventricular apex and the atrium. Specifically, the SA node in the atrium can be contacted by electrode band 48 as the bent portion 53 of the stylet 40 approaches the same. Furthermore, as the J-shaped tip 55 of the stylet 40 approaches the distal end 16 of the flexible member 12, the tip of the flexible member curves so that the electrode cap 46 secured thereto can be properly positioned in the ventricular apex.

The present invention may be embodied in other forms without departing from the spirit or essential attributes thereof and accordingly reference should be made to the claims rather than to the foregoing specification as indicating the scope thereof.

What is claimed is:

1. A steerable catheter comprising:

an elongated flexible member having a proximal end and a distal end, said flexible member further having a plurality of lumens, each of said lumens extending from said proximal end to said distal end thereof;

a stylet having a first end and a second end, said stylet being insertable in one of said lumens, said stylet further having a bent portion formed along the length thereof, and a J-shaped tip adjacent said first end, said bent portion and said tip causing segments of said flexible member in contact with said bent portion and said tip to bend;

a plurality of electrode means secured around the periphery of said flexible member in a predetermined pattern, and a plurality of electrical leads, each of said electrical leads extending through said proximal end of said flexible member and through a corresponding one of said plurality of lumens, said electrical leads being connected to said electrode means.

2. The catheter of claim 1 further including a manifold extending outwardly from said proximal end of said flexible member, and wherein each of said electrical leads partially extends through said manifold into a corresponding one of said plurality of lumens.

3. The catheter of claim 1 further including a stylet tube extending proximally from one of said lumens, said stylet being insertable through said stylet tube and into said lumen.

4. The catheter of claim 1 wherein said electrode means includes an electrode cap secured around said distal end of said flexible member and an electrode band secured around said flexible member and spaced from said electrode cap.

5. A steerable catheter comprising:

an elongated flexible member having a proximal end and a distal end, said flexible member having a J-shaped tip located adjacent said distal end thereof, said flexible member further having a plurality of lumens, each of said lumens extending from said proximal end to said distal end thereof;

a stylet having a first end and a second end, said stylet being insertable in one of said lumens, said stylet further having a first bent portion formed along the length thereof, and a second bent portion which is offset from said first bent portion, said first and second bent portions causing said tip of said flexible member to rotate as said first and second bent portions approach said tip through said lumen therein;

a plurality of electrode means secured around the periphery of said flexible member in a predetermined pattern, and a plurality of electrical leads, each of said electrical leads extending through said proximal end of said flexible member and through a corresponding one of said plurality of lumens, said electrical leads being connected to said electrode means.

6. The catheter of claim 5 further including a manifold extending outwardly from said proximal end of said flexible member, and wherein each of said electrical leads partially extends through said manifold into a corresponding one of said plurality of lumens.

7. The catheter of claim 5 further including a stylet tube extending proximally from one of said lumens, said stylet being insertable through said stylet tube into said lumen.

8. The catheter of claim 7 wherein said electrode means includes an electrode cap secured around said distal end of said flexible member and an electrode band secured around said flexible member and spaced from said electrode cap.

* * * * *